United States Patent [19]

Beier et al.

[11] Patent Number: 4,571,182

[45] Date of Patent: Feb. 18, 1986

[54] ARRANGEMENT FOR CARRYING DENTAL IMPLEMENTS

[75] Inventors: Stefan Beier, Biberach; Franz-Xaver Boeckh, Schoneburg; Anton Braun; Thomas Brunner, both of Biberach; Dieter Hoffmann, Schemmerhofen; Peter Kiess, Mittelbiberach; Bernd Wagner; Heiner Zinser, both of Biberach, all of Fed. Rep. of Germany

[73] Assignee: Kaltenbach & Voigt GmbH & Co., Fed. Rep. of Germany

[21] Appl. No.: 573,827

[22] Filed: Jan. 24, 1984

[30] Foreign Application Priority Data

Jan. 24, 1983 [DE] Fed. Rep. of Germany ....... 3302189

[51] Int. Cl.⁴ .............................................. A61C 1/14
[52] U.S. Cl. ..................................................... 433/79
[58] Field of Search ........................................... 433/79

[56] References Cited

U.S. PATENT DOCUMENTS 3,160,379 12/1964 Gardella .................................. 433/79
3,890,096 6/1975 Nichol et al. ........................ 433/79
4,179,813 12/1979 Runnells et al. ...................... 433/79
4,445,859 5/1984 Hoftmeister et al. ................. 433/79

Primary Examiner—Robert Peshock
Attorney, Agent, or Firm—Scully, Scott, Murphy & Presser

[57] ABSTRACT

An arrangement for the carrying of dental implements, consisting of a carrying plate arranged on a supporting member, and which has one side facing upwardly including positioning elements provided for the implements on the upwardly facing plate side thereof. The dental implements which are located on the support plate can consist of hand instruments, for example, probes, mirror, tamping instruments, pincettes or the like. Furthermore, the implements can also be formed of cotton receptacles, medication flasks, waste receptacles, as well as worktool, handpiece and anglepiece supports. The positioning elements for the implements can be arranged directly on the carrying plate or also in flat trays, or can even be formed by the flat trays themselves. As the result of an inclination or supplying relative to the horizontal of the upper surface of the carrying plate, the implements which are arranged thereon can be readily surveyed by the dentist or the assistant, and without having to reach thereover, can be easily directly passed over with the hand or by means of a pincette or forceps, or the like.

17 Claims, 28 Drawing Figures

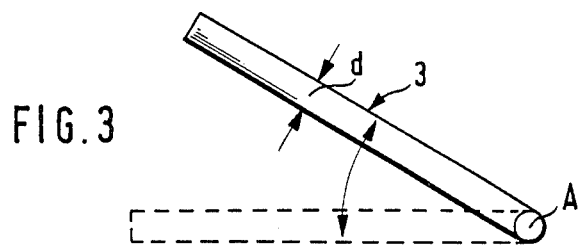
FIG.3
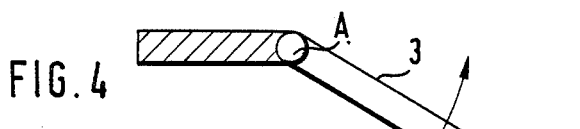
FIG.4
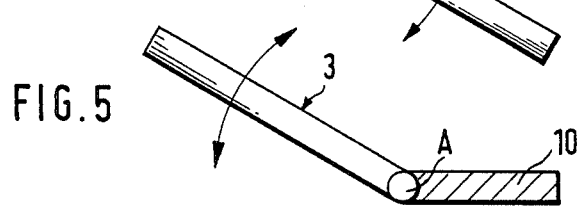
FIG.5
FIG.6
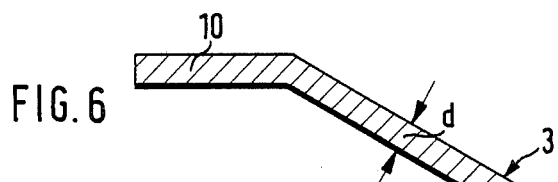
FIG.7
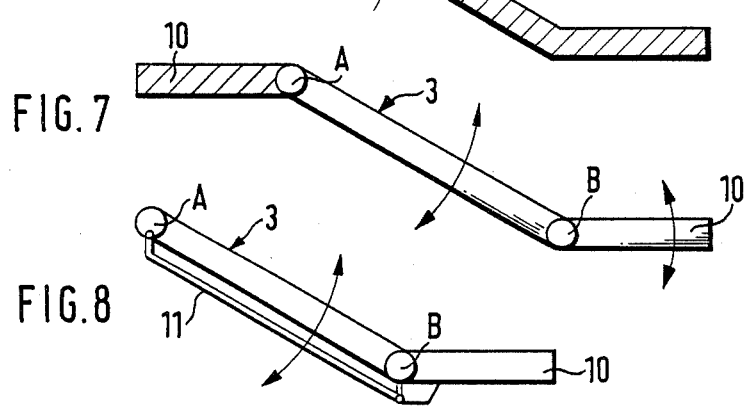
FIG.8
FIG.9
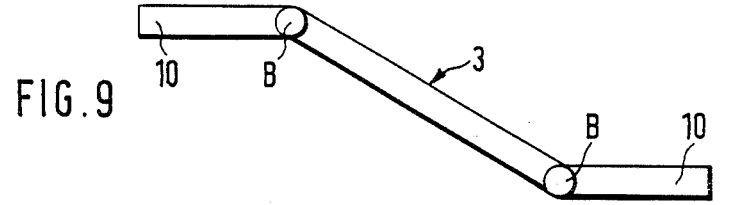

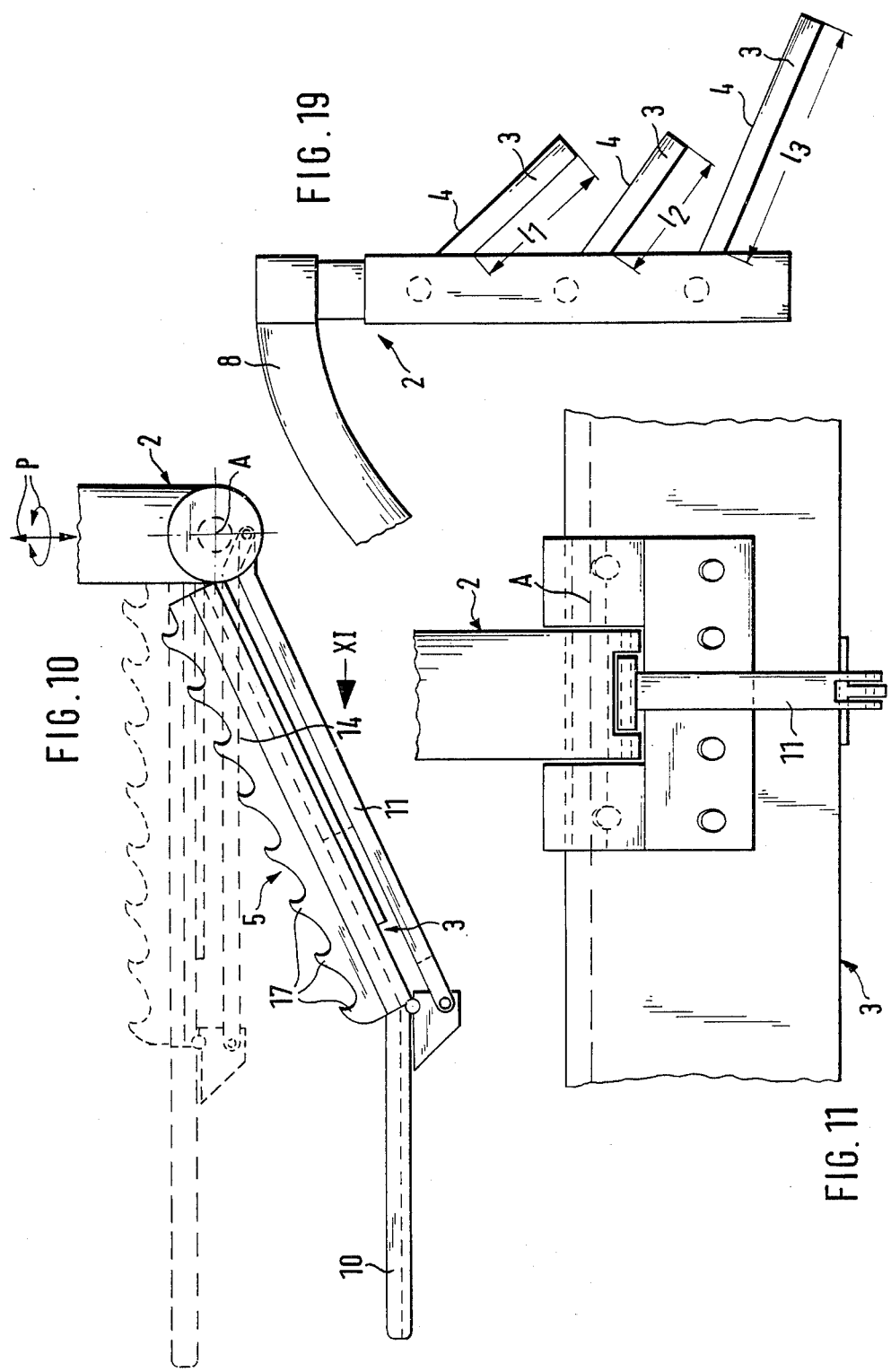

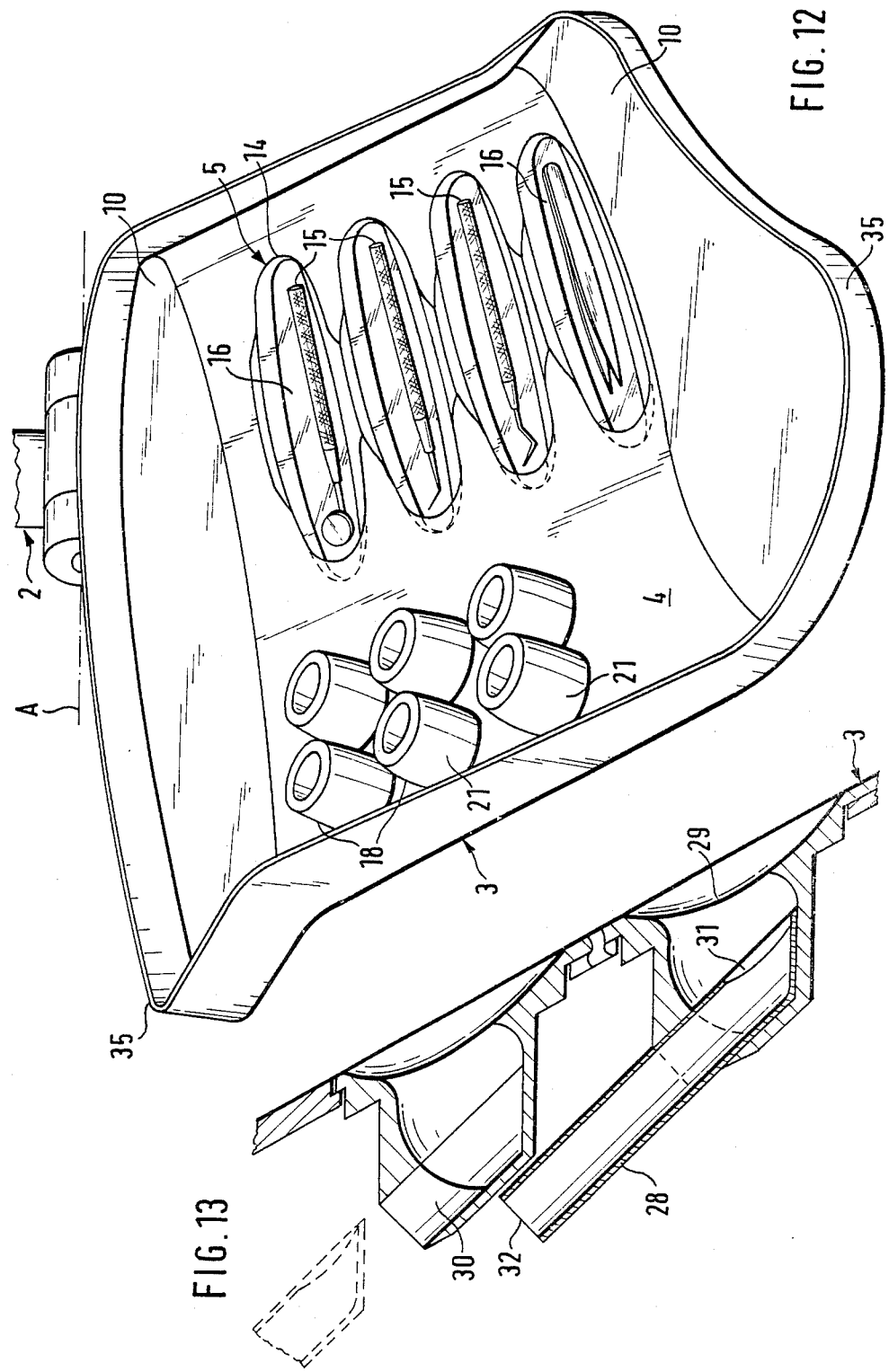

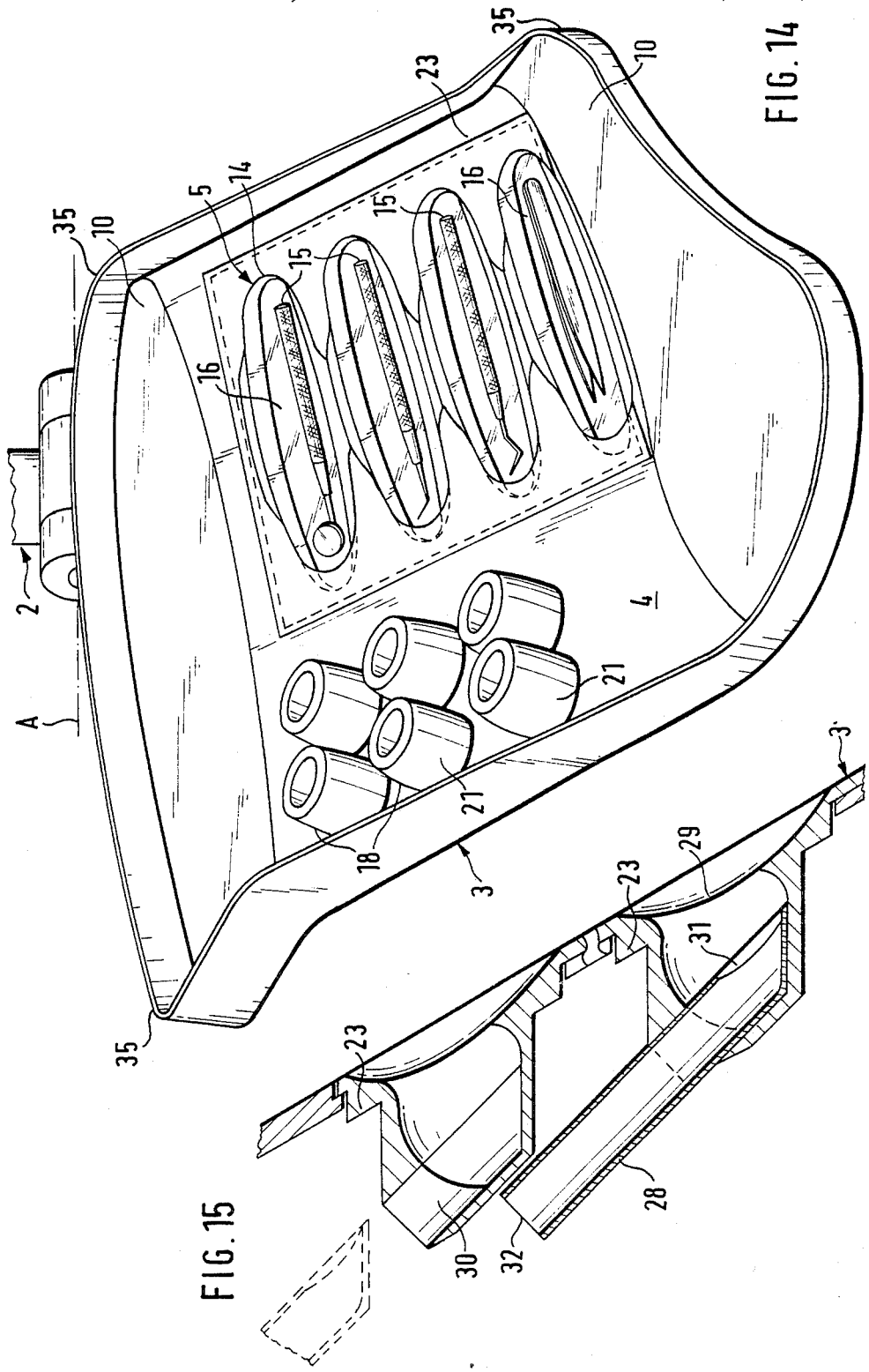

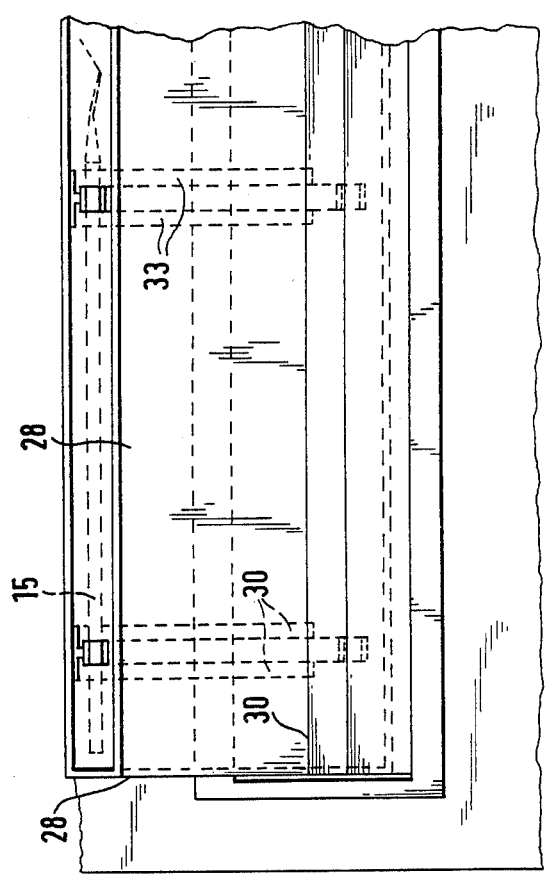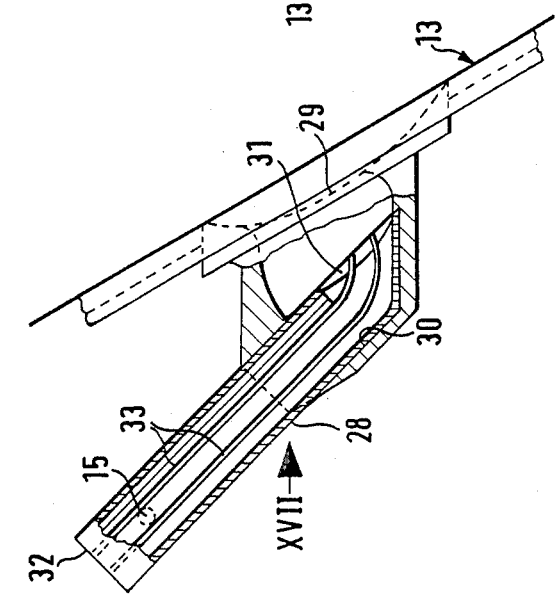

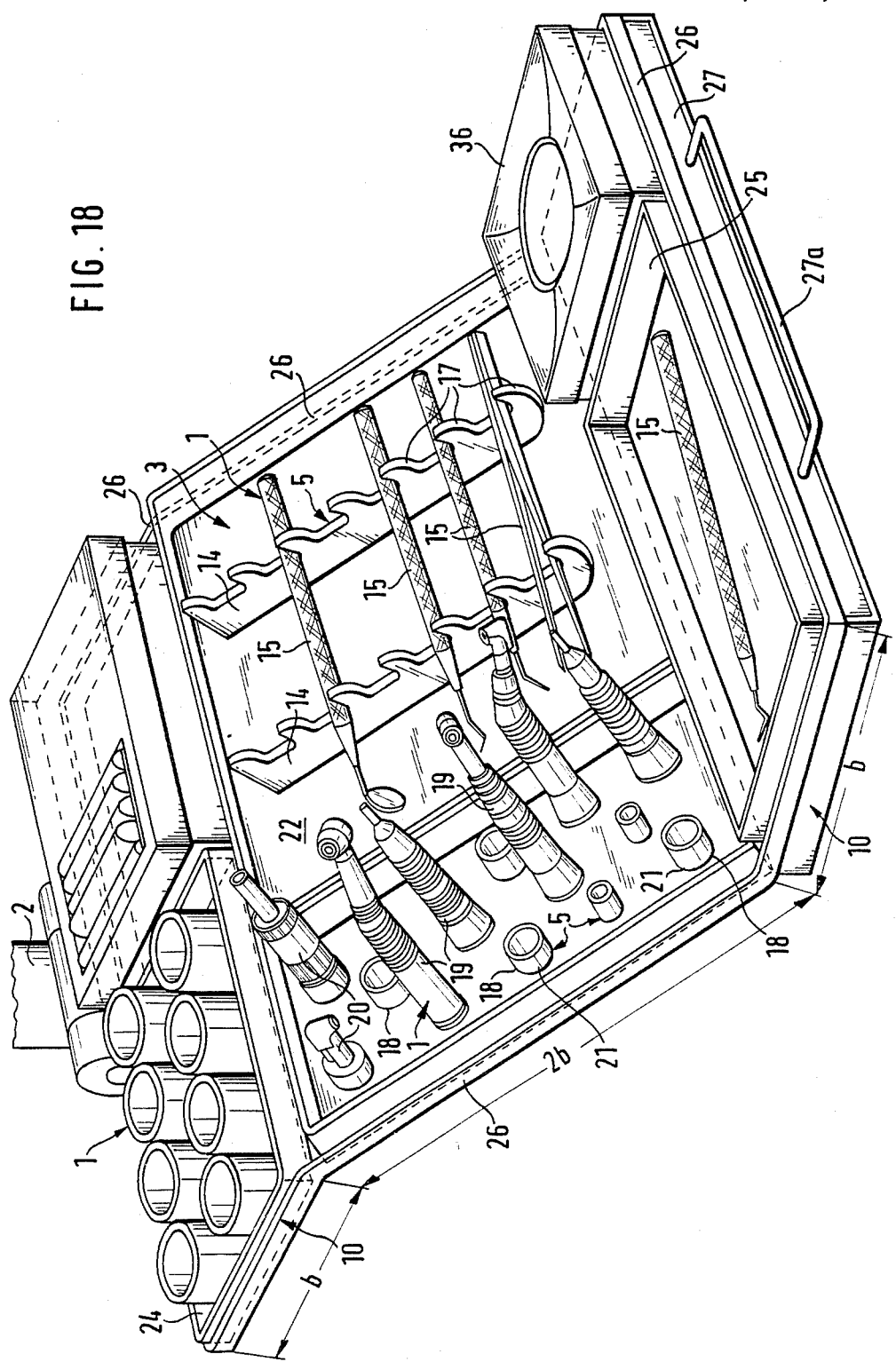

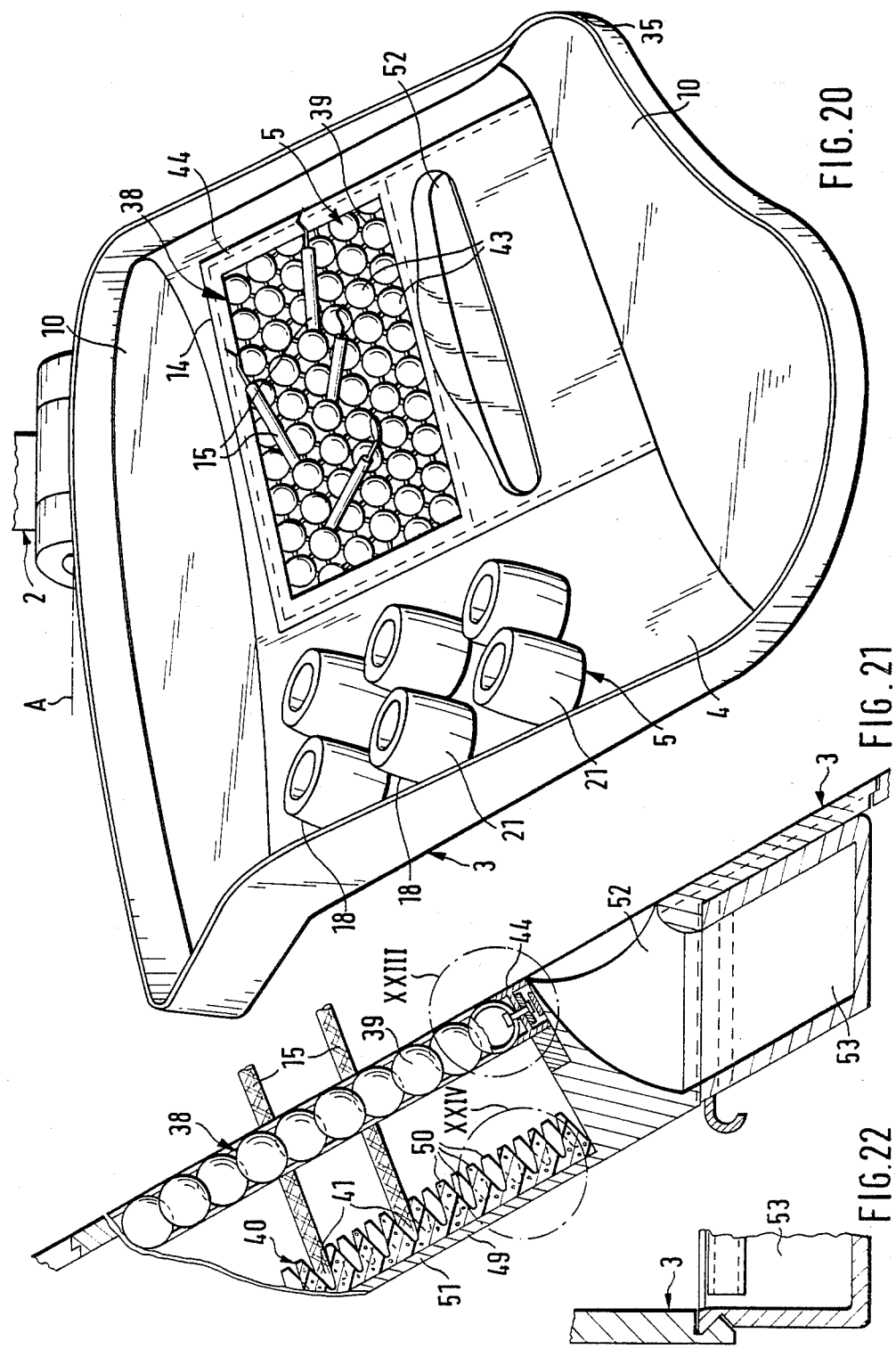

ARRANGEMENT FOR CARRYING DENTAL IMPLEMENTS

BACKGROUND OF THE INVENTION

1. Field of the Invention

The present invention relates to an arrangement for the carrying of dental implements, consisting of a carrying plate arranged on a supporting member, and which has one side facing upwardly, including positioning means provided for the implements on the upwardly facing plate side thereof. The dental implements which are located on the support plate can consist of hand instruments, for example, probes, mirror, tamping instruments, pincettes or the like. Furthermore, the implements can also be formed of cotton receptacles, medication flasks, waste receptacles, as well as worktool, handpiece and anglepiece supports. The positioning means for the implements can be arranged directly on the carrying plate or also in flat trays, or can even be formed by the flat trays themselves.

2. Discussion of the Prior Art

An arrangement of the above-mentioned type is known, for example, from the brochure "Systematic 1021/A" PR-No. 7398VI.73, published by the Kaltenbach & Voigt GmbH & Co. In this known arrangement, the carrying plate is arranged horizontally on the supporting member so that the upper surface thereof which includes the positioning means will also extend horizontally. This horizontal arrangement has the result that the dentist or the assistant can only with difficulty, reach any implements which are located towards the rear on the carrying plate, inasmuch as the implements which located in a region which is further towards the front, must be reached over, and it can occur that the view of the rearwardly located implements can be blocked by the frontwardly located implements, which will render more difficult any surveying thereof and will frequently require the undertaking of a timeconsuming search for a certain implement.

SUMMARY OF THE INVENTION

Accordingly, it is an object of the present invention to overcome the foregoing disadvantages through the provision of an arrangement of the above-mentioned type, which will facilitate an unhindered access to and a good survey over the implements which are arranged on the carrying plate.

The advantages which are achieved through intermediary of the present invention can be essentially ascertained in that as the result of an inclination or supplying relative to the horizontal of the upper surface of the carrying plate, the implements which are arranged thereon can be readily surveyed by the dentist or the assistant, and without having to reach thereover, can be easily directly passed over with the hand or by means of a pincette or forceps, or the like.

BRIEF DESCRIPTION OF THE DRAWINGS

Reference may now be had to the following detailed description of exemplary embodiments of the invention, taken in conjunction with the accompanying drawings; in which:

FIG. 3 illustrates a generally diagrammatic representation of a carrying plate which is pivotable above a horizontal axis;

FIGS. 4 and 5 each, respectively, illustrate views similar to FIG. 3 of modified embodiments;

FIG. 6 illustrates a diagrammatic representation of a non-pivotable carrying plate;

FIG. 7 illustrates a diagrammatic representation of a carrying plate which is pivotable about two horizontal pivoting axes;

FIGS. 8 and 9, respectively, illustrate views similar to that of FIG. 7 of modified embodiments thereof;

FIG. 10 illustrates a side view of a carrying plate which is equipped with an extension plate and a parallelogram linkage;

FIG. 11 illustrates a carrying plate of FIG. 10 in a view taken in the direction of Arrow XI in FIG. 10;

FIG. 12 illustrates, on an enlarged scale, a modified embodiment of the arrangement of FIG. 1;

FIG. 13 illustrates a sectional view of a detail in FIG. 12;

FIG. 14 illustrates a modified embodiment in a view similar to that of FIG. 12;

FIG. 15 illustrates a sectional view of a detail in FIG. 14;

FIG. 16 illustrates a modified embodiment in a view similar to that in FIG. 15;

FIG. 17 illustrates a view of the carrying plate of FIG. 16 taken in the direction of Arrow XVII in FIG. 16;

FIG. 18 illustrates an embodiment which is modified with respect to that shown in FIGS. 12 and 14;

FIG. 19 illustrates a diagrammatic representation of three carrying plates which are arranged one above the other;

FIG. 20 illustrates an embodiment which is modified with respect to that shown in FIGS. 12, 14 and 18;

FIG. 21 illustrates a portion of the carrying plate of the embodiment of FIG. 20, shown in a longitudinal section on an enlarged scale;

FIG. 22 illustrates a sectional view through the lower portion of the carrying plate of FIG. 21;

DETAILED DESCRIPTION

Figure 1:
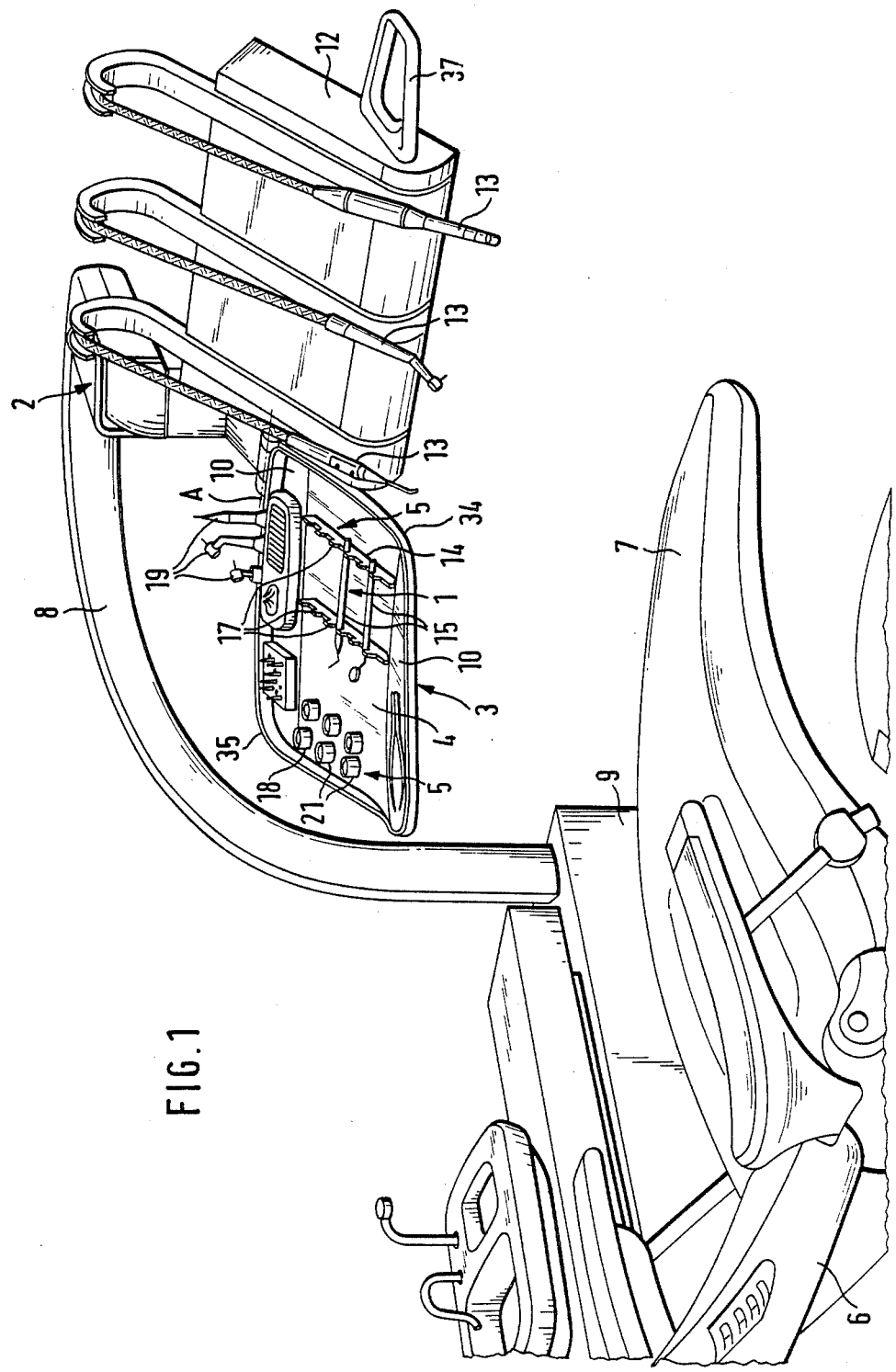
FIG. 1 illustrates a perspective representation of an inventive carrying plate which is arranged adjacent to a support for hose-connected handpieces, and which forms the arrangement for the carrying of dental implements.

The arrangement for the carrying of dental implements 1 consist of carrying plate 3 having an upwardly facing side 4, and which is mounted on a supporting member 2. Provided on the upwardly facing plate surface 4 are positioning means 5 for the dental implements 1.

The carrying plate 3 is arranged on the supporting member 2 in a manner such that the surface 4 which incorporates the positioning means 5 is inclined or angled relative to the horizontal.

The carrying plate 3 can hereby have a horizontal lower side. However, it is spacesaving when, as illustrated, the carrying plate 3 has the same thickness d throughout, and the plate itself is mounted inclined on the supporting member, inasmuch as thereby the carrying plate 3 can be moved into a portion closely above the patient, which is readily accessible to the dentist or an assistant, or which faces towards the dentist or the assistant.

The carrying plate 3 is arranged so as to be movable on the supporting member 2, such that it can be moved into a position facing with the plate surface 4 incorporating the positioning means towards the backrest 6 of a treatment chair 7 which is associated with the carrying plate 3. In this manner, the carrying plate together with the above-mentioned plate surface 4, can also be accessible to the dentist who is mostly seated behind thereof.

The supporting member 2 is formed by a support arm 8 of a dental equipment stand 9. The supporting member 2 can be arranged so as to be movable in all directions, and/or the carrying plate 3 movably arranged on the supporting member 2, so as to be; for example, vertically or horizontally adjustable.

In order to change the inclination from the horizontal or the angle of the carrying plate 3; in effect the upper side 4 of the carrying plate 3, the carrying plate 3 is connected with the supporting member 2 so as to be pivotable about a horizontal axis A.

For example, in the embodiments pursuant to FIGS. 1, 2, 7, 9, 12, 14 and 18, the carrying plate 3 incorporates an extension plate 10 at respectively each of its upper and lower edge. In the embodiments pursuant to FIGS. 5, 8 and 10, such an extension plate 10 is provided only at the lower edge of the carrying plate 3. For example, as can be ascertained from FIG. 18, the extension plates 10 can serve, for instance, for the carrying of certain implements 1; for example, the upper extension plate 10 can serve for the carrying of containers, such as cotton receptacles, medication receptacles or the like, and the lower extension plate 10 for the repository of used instruments 15, or for the carrying of a waste container 36.

Pursuant to FIG. 9, the extension plates 10 can be slightly inclined or tilted relative to the horizontal. In the other embodiments, the at least one extension plate 10 is positioned horizontally.

As can be ascertained from FIGS. 7, 8 and 9, the at least one extension plate 10 is connected with the carrying plate 3 so as to be pivotable about a horizontal axis B. The carrying plate 3 of the at least one extension plate 10 can be fixed in the assumed position of movement. The different capabilities of the arrangement with respect to the displaceability of the carrying plate 3 or of the at last one extension plate 10, are diagrammatically illustrated in FIGS. 3 through 5 and 7 through 9. FIG. 6 illustrates an arrangement of a carrying plate 3 or extension plate 10 which is not pivotable.

In order to ensure the extension plate 10 of maintaining its horizontal position during a pivotal displacement of the carrying plate 3 pursuant to FIGS. 8, 10, and 11, the supporting member 2, or in a given instance the extension plate 10 adjoining the supporting member, is connected through a parallelogram linkage 11 arranged below the carrying plate 3, with the extension plate 10 located along the edge of the carrying plate which is remote from the supporting member or from the extension plate neighboring the supporting member 2. This construction can be clearly ascertained from FIGS. 10 and 11. In FIG. 10 there are illustrated the possibilities for movement of the supporting member 2 by means of arrows P.

Figure 2:
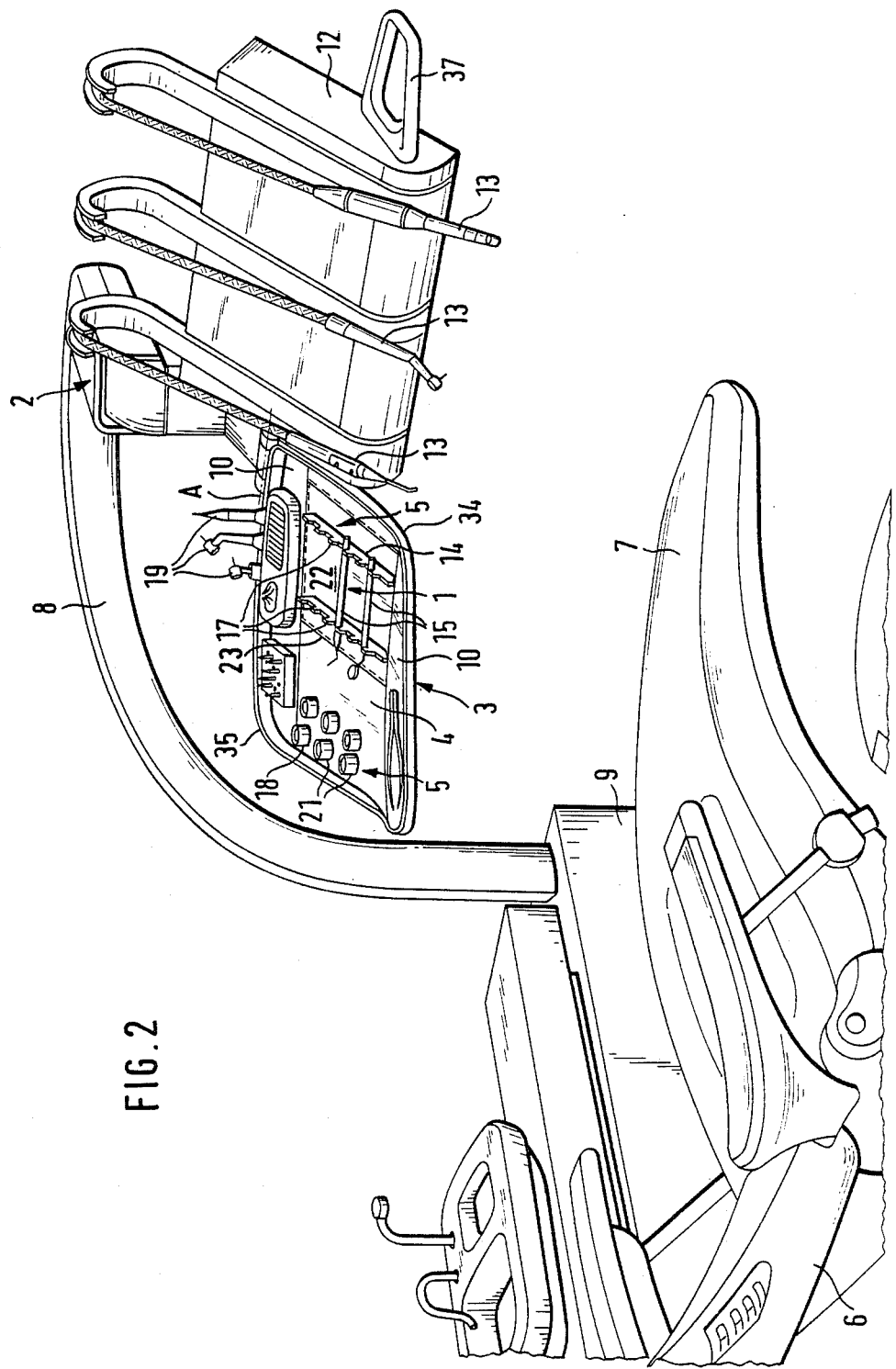
FIG. 2 is a view similar to that of FIG. 1 illustrating a modified embodiment of the invention.

In the embodiments pursuant to FIGS. 1 and 2, the carrying plate 3 is arranged closely to a holder 12 on the supporting member 2 for hose-connected dental handpieces 13.

As can be ascertained from FIGS. 1, 2, 12 14, 17 and 18, the positioning means 5 which, in the viewing direction are located towards the front right-hand, are constituted of depositing elements 14 for the implements 1 which are formed from elongated instruments 15; for instance, probes, pincettes or forceps, or the like. The depositing element 14 hereby consists of support cradles which, for example, pursuant to FIGS. 12 and 13, are formed by indentations 16. The support cradles presently serve for the receipt of one type of instrument 15, for example, oral mirrors. For this purpose there are provided three to four indentations 16 for elongated instruments 15, whereby these elongated indentations 16 extend in parallel with the edge of the carrying plate 3 which is connected to the supporting member 2.

In the embodiments disclosed in FIGS. 1, 2, 10 and 18, the support cradles are formed through at least two parallel spaced rows of retaining cogs 17, wherein the retaining caps 17 of each row are spaced from each other through the formation of a receiving tine for presently one end of an instrument 15.

In the embodiments pursuant to FIGS. 12, 14 and 18, the positioning means 5 consist of holders 18 for dental handpieces 19 which are separated from a supply hose or a connecting piece, such as, for instance, drill handpieces implements, formed by their drives, drill heads or other components 20. The mentioned holders 18 are hereby formed through insert or attachment socket sleeves 21.

In the embodiments according to FIGS. 1 and 12, the positioning means 5 are provided directly on the upwardly facing side 4 of the carrying plate 3. However, another possibility is illustrated in FIGS. 2, 14 and 18, pursuant to which the positioning means 5 on the upwardly facing side 22 are the bottoms of flat trays 23 on the upwardly facing side 4 of the carrying plate 3. Obtainable hereby is an economical arrangement of the trays 23 with respect to their placing positions, wherein the trays evidence primarily normal dimensions when, pursuant to FIG. 18, the measurement 2b of the carrying plate 3 in the direction from the supporting member 2 is approximately twice as large as the dimension b of the at least one extension plate 10 in the same direction. Similar relationship reign in the transversely extending direction.

As can be ascertained in particular from FIG. 18, receiving trays 24 or depositing trays 25 are provided on the extension plates 10. Hereby, the carrying plate 3 or the at least one extension plate 10, is provided with retaining elements 26 for the trays 23 or 24, 25. These retaining elements 26 are formed by rim rails which are extend about the plate edges. For example, when pursuant to FIG. 1, no trays are provided, then the rim rails serve as a security for the implements 1 which are located on the plates 3 or 10.

In the embodiment pursuant to FIG. 18, provided in the extension plate 10 which is fastened to the edge of the carrying plate 3 remote from the edge with the extension plate proximate the supporting element 2, is a drawer 27 with a handle 27a which, for example, serves as a discard drawer, for instance, for used instruments 15, or for cotton or the like.

In the embodiments pursuant to FIGS. 12 through 17, the depositing elements 14 can have a refill magazine 28 associated therewith for receiving a supply of horizontally positioned elongated instruments 15. The refill magazine 28 is provided on the downwardly facing side of the carrying plate 3, wherein each individual depositing element 14 has a special refill magazine 28 associated therewith. Thereby, the carrying plate 3 is presently provided with a through-opening 29 communicating the depositing element 14 with the refill magazine 28 for the through-passage of the instruments 15. On the downwardly facing side of the carrying plate, connected to the through-opening 29 is an upwardly opening horizontal insert slot 30 for the removable, cassette-like refill magazine 28. In FIGS. 13 and 15, the refill magazine 28 is illustrated by means of phantom-lines in a position shortly prior to the insertion into the insert slot 30. Below, on the side facing towards the carrying plate 3, the refill magazine 28 possesses an outlet opening 31 facing towards the through-opening 29 in the carrying plate 3, for the transfer of the instruments 15 from the refill magazine into the depositing element 14 which is presently formed by an indentation 16.

At its upper end, the refill magazine possesses a refill opening 32 for its refilling with elongated instruments 15. As can be ascertained from FIGS. 16 and 17, the refill magazine is provided interiorly thereof with guide bars 33 which are arranged to provide a spacing therebetween conforming generally to about the thickness of the instruments 15. These guide bars 33 serve to guide the downwardly dropping refilled instruments through the refill opening 32. The guide bars 33 are arranged along the inner walls over the width of the refill magazine 28 and are presently located in the regions at both ends of the instruments 15.

. In the embodiments pursuant to FIGS. 20 through 29, the depositing elements 14 are formed through an insert or plug-in arrangement 38 for the elongated instruments 15. This has the advantage that the instruments 15 project to a predetermined extent from the upper side 4 of the carrying plate 3 and, at least in some instances of operation, will be particularly accessible for engagement by the dentist or the assistant.

The insert arrangement 38 can be formed, for example, by means of a foamed material layer or through a bristle mat with bristles extending essentially perpendicular away from the upwardly facing side 4 of the carrying plate 3. In the embodiments pursuant to FIGS. 20, 21, 23, 26, 27 and 28, the insert arrangement 38 is formed by a piercing layer 39 provided in the upwardly facing side of the carrying plate 3, which permits passage therethrough of the instruments 15 in their longitudinal extensions. According to FIGS. 21, 24, and 25, a fixing or positioning layer 40 for the extended through ends 41 of the instruments 15 is located below the piercing layer 39. The fixing layer 40 is arranged at a spacing from the through-piercing layer 39.

Figure 26:
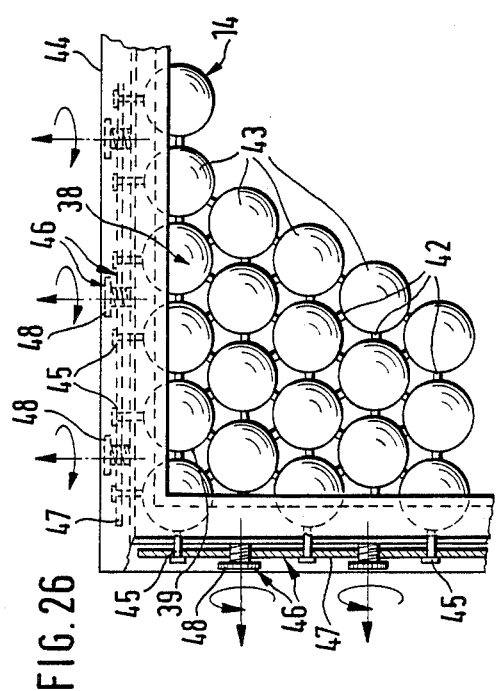
FIG. 26 illustrates a top plan view, on an enlarged scale, of a detail of FIG. 20.
Figure 28:
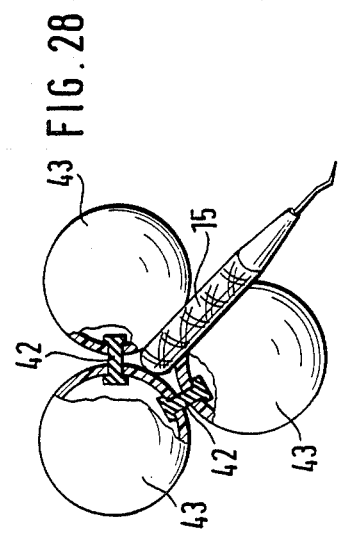
FIG. 28 illustrates a segment of FIG. 26 on an enlarged scale.

As can be ascertained particularly from FIGS. 26 and 28, the through-piercing layer 39 is formed by restraining members 43 arranged with their meridian circles in one plate and essentially movable apart within this plane against the action of elastic restoring force elements 42 and maintained against each other under the effect of these restoring force elements 42. The instruments 15 are hereby pushed through within the interspaces present intermediate the restraining members. The restraining members 43 can be constituted of metal or plastic material, and are formed of balls or spheres. The restoring force elements 42 which are provided intermediate the restraining members 43 can be formed through rubber connecting webs or also through tension springs.

Figure 27:
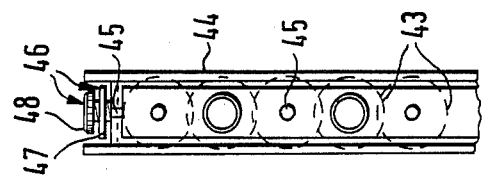
FIG. 27 illustrates a side view of the detail in FIG. 26.
Figure 23:
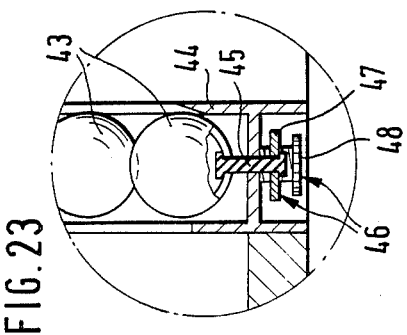
FIG. 23 illustrates, on an enlarged scale, the section shown in FIG. 21 as designated by XXIII.

As can be ascertained from FIGS. 23, 26 and 27, buffer or shock-absorbing members 45, for example, rubber pins, are arranged between the restraining members 43 which are located pins, are arranged between the restraining members 43 which are located at the edge of the piercing layer 39 and a frame encompassing the edges of the piercing layer. The buffer members 45 have prestressing means 46 associated therewith, which consists of a prestressing bar 47 traversing the buffer members 45, whose distance from the edge of the piercing layer 39 is adjustable by means of adjusting elements 48, for example, screws, which are supported on the frame 44. When the screws 48 are displaced, for instance in the direction of the curved arrows ascertainable in FIG. 26 then the prestressing bars 47 will displace in the direction of the straight arrows and thereby more or less stress the buffer members 45, which will also exert an effect on the restoring force members 42.

Figure 25:
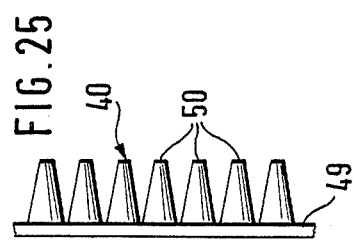
FIG. 25 illustrates a sectional view of FIG. 24.
Figure 24:
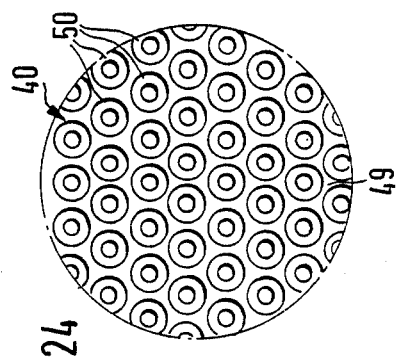
FIG. 24 illustrates, on an enlarged scale, the section shown in FIG. 21 as designated by XXIV.

Pursuant to FIGS. 21, 24, and 25, the fixing layer 40 is arranged on a base support 49. The fixing layer 40 can consist of a foamed material layer or the like, or also of a bristle mat with bristles which are essentially directed perpendicular to the upwardly facing side of the carrying plate 3. In accordance with FIGS. 21, 24 and 25, the fixing layer 40 is formed by protuberances 50 which are spaced from each other at least at their upper ends and which are arranged on the base support 49 so as to extend towards the upwardly facing side 4 of the carrying plate 3, so that the interspaces between the protuberances 50 serve for the receipt and, as a result, for the fixing of the ends 41 of the instruments 15 which extend through the piercing 39. The protuberances 50 reduce in size towards the upwardly facing side of the carrying plate 3, and are formed in the type of knubs, cones, truncated cones or the like. The protuberances 50 are hereby arranged closely adjacent to each other.

In the embodiment pursuant to FIG. 21, the carrying plate 3 is constructed to be hollow, whereby the base support 49 which supports the fixing layer 40 is formed by the bottom 51 of the hollow carrying plate 3. The base support 49 with the fixing layer 40 can, however, also be arranged as a separate component on the bottom 51 of the hollow carrying plate 3.

In the embodiments according to FIGS. 20 through 22, provided in the upwardly facing side of the carrying plate 3, is a discarding opening 52 for used implements 1; for example, for used instruments 15. The discarding opening 52 is hereby located adjacent the insert arrangement 38. In the carrying plate 3 there is provided a discard drawer 53 which is associated with the discarding opening 52 and located therebelow.

FIG. 19 illustrates an embodiment in which a plurality of carrying plate 3 are arranged one above the other on the supporting member 2. Thereby, the sides 4 of the superposed carrying plates 3, or the carrying plates 3 themselves, each have a different degree inclination from the horizontal wherein the sides incorporate the positioning means 5, in order to facilitate an individual correlation with the current treatment relationships. For the same reason, the superposed carrying plates 3, measured along their dimension extending away from the supporting member 2, each possess a different length ($l_1, l_2, l_3$). This length can be variable; for example, in that the carrying plates 3 are supported on the supporting member 2 so as to be displaceable in parallel relative to each other, which is also applicable to the case in which only a single carrying plate is provided; for example, pursuant to FIG. 13.

Pursuant to FIGS. 1 and 2, the corners 34 of the carrying plate 3 are rounded off. From FIGS. 1, 2, 12 and 14 there can be ascertained that also the outer corner 35 of the at least one extension plate 10 is rounded off. Through this rounding off there is achieved that the carrying plate 3 can be moved still closer the patient, in particular when at least one of the lower extension plate 10, as indicated in FIGS. 1 and 2, has a triangular base configuration.

Designated with reference numeral 37 is a handle grip which is provided on the holder 12 for effecting the movement of the holder 12 and, as required, also of the carrying plate.

What is claimed is:

1. In an arrangement for carrying dental implements adajacent a dental treatment chair, and including a supporting member, and a carrying plate mounted on the supporting member, and having an upwardly facing side and positioning means located on the upwardly facing side for holding the implements, the improvement comprising:

the upwardly facing side of the carrying plate is inclined relative to the horizontal and faces toward a backrest of the adjacent dental treatment chair;

the carrying plate is moveably mounted on a support arm of a dental equipment stand;

at least one extension plate an an edge of the carrying plate, arranged to extend in a horizontal position, and connected to the carrying plate for pivotal movement relative to the carrying plate about a horizontal axis; and wherein the carrying plate and the extension plate are restrainable in assumed positions of movement.

2. Arrangement as claimed in 1, wherein said supporting member or another extension plate adjacent said supporting member is connected through a parallelogram linkage with said one extension plate, which is located at an edge of the carrying plate which is remote from the supporting member or from said other extension plate.

3. Arrangement as claimed in claim 1, wherein said carrying plate is arranged besides a holder for hose-connected dental handpieces on said supporting member.

4. Arrangement as claimed in claim 1, wherein said positioning means comprise support means for implements constituted of elongated instruments.

5. Arrangement as claimed in claim 4, wherein the positioning means are formed by at least two parallel rows of detents spaced from each other, each detent forming a receiving tine for holding one end of an instrument.

6. Arrangement as claimed in claim 4, wherein the support means are formed by an inserting arrangement for the elongated instruments.

7. Arrangement as claimed in claim 6, wherein the inserting arrangement comprises a piercing layer on the upwardly facing side of the carrying plate to permit passage therethrough of the instruments, and a fixing layer positioned on a base support and located below the piercing layer for receiving the inserted ends of the instruments.

8. Arrangement as claimed in claim 6, wherein the inserting arrangement comprises a piercing layer on the upwardly facing side of the carrying plate to permit passage therethrough of the instruments, the piercing layer including a multitude of restraining members arranged in a plane, moveable apart from each other, and connected together by a multitude of elastic restoring force elements, shock-absorbing means, such as rubber pins, arranged between the restraining members along the edge of the piercing layer and on a frame encompassing the edges of said piercing layer, and prestressing means associated with said shock-absorbing means.

9. Arrangement as claimed in claim 1 wherein:

a plurality of carrying plates are mounted on the support arm, each carrying plate having an upwardly facing side and positioning means located on said upwardly facing side for holding the implements;

the carrying plates are arranged one above the other; and the upwardly facing sides of the carrying plates are inclined at different degrees relative to the horizontal.

10. Arrangement as claimed in claim 1, comprising a discharge opening for used implements being provided in the upwardly facing side of the carrying plate.

11. Arrangement as claimed in claim 10, wherein the carrying plate includes a discharge drawer communicating with the discharge opening.

12. Arrangement as claimed in claim 1, wherein the positioning means comprise holders for dental handpieces which are separated from a supply hose, or implements forming connecting pieces, drive heads or other components thereof.

13. Arrangement as claimed in claim 1, wherein the dimension of the carrying plate in the direction away from the supporting member is approximately twice as large as the dimension of the at least one extension plate in the same direction.

14. Arrangement as claimed in claim 1, wherein receiving trays or depositing trays are arranged on said at least one extension plate.

15. Arrangement as claimed in claim 4, further comprising a refill magazine arranged below a downwardly facing side of the carrying plate for receiving a supply of elongated instruments.

16. Arrangement as claimed in claim 15, wherein said carrying plate includes a through-opening in communication with the refill magazine to pass the elongated instruments from the refill magazine to the upwardly facing side of the carrying plate.

17. Arrangement as claimed in claim 16 wherein the side of the refill magazine facing towards the carrying plate includes a discharge opening facing the through-opening in the carrying plate to discharge instruments from the refill magazine onto the carrying plate.

* * * * *